Figure 1:
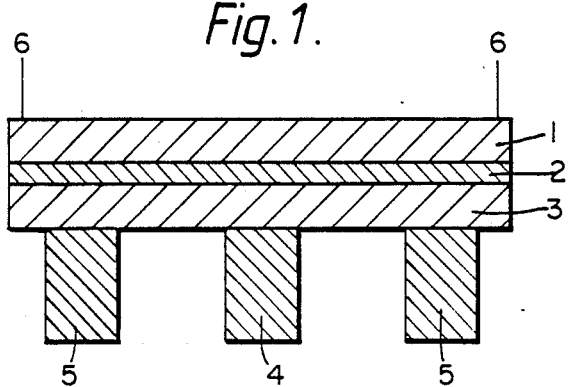

United States Patent [19]

Vadgama

[11] Patent Number: 4,886,740
[45] Date of Patent: Dec. 12, 1989

[54] ENZYME-ELECTRODE SENSOR WITH ORGANOSILANE TREATED MEMBRANE

[75] Inventor: Pankaj M. Vadgama, Newcastle-Upon-Tyne, England

[73] Assignee: Imperial Chemical Industries PLC, London, England

[21] Appl. No.: 867,439

[22] Filed: May 28, 1986

[30] Foreign Application Priority Data

Jun. 5, 1985 [GB] United Kingdom ............... 8514176

[51] Int. Cl.⁴ .................. C12Q 1/00; G01N 27/26
[52] U.S. Cl. ............................... 435/4; 435/25; 435/174; 435/179; 435/288; 435/817; 436/72; 204/403; 204/415; 204/418; 204/1 T
[58] Field of Search ............... 204/418, 403, 1 T, 415; 435/4, 25, 174, 179, 288, 817; 436/72

[56] References Cited

U.S. PATENT DOCUMENTS

| | | |
|---|---|---|
| 3,539,455 | 11/1970 | Clark, Jr. . |
| 3,979,274 | 9/1976 | Newman . |
| 4,240,889 | 12/1980 | Yoda et al. ............... 435/817 X |
| 4,384,045 | 5/1983 | Ho et al. ............... 435/175 X |
| 4,581,336 | 4/1986 | Malloy et al. ............... 435/176 |

FOREIGN PATENT DOCUMENTS 2036499 2/1972 Fed. Rep. of Germany .

OTHER PUBLICATIONS

Clark et al.; Annals New York Academy of Sciences; "Electrode Systems for Continuous Monitoring in Cardiovascular Surgery", vol. 102, pp. 29–45 (1962).

Primary Examiner—Robert J. Warden
Assistant Examiner—Richard Wagner
Attorney, Agent, or Firm—Cushman, Darby & Cushman

[57] ABSTRACT

A membrane for an enzyme-electrode type sensor treated to increase the range of linearity of the sensor response.

6 Claims, 2 Drawing Sheets

ENZYME-ELECTRODE SENSOR WITH ORGANOSILANE TREATED MEMBRANE

MEMBRANE

This invention relates to a membrane treated to improve its properties, to a method for treating a membrane, to a sensor of the enzyme-electrode type comprising a treated enzyme and to an analytical method using an enzyme-electrode type sensor comprising a treated membrane.

Enzyme electrodes are increasingly used in medical and other laboratories particularly for the determination of materials such as glucose and urea in specimens of blood and other physiological fluids. Such electrodes are described in many publications notably an article by Clark and Lyons (Annals of the New York Academy of Sciences, 102, 29–45, 1962) and U.S. Pat. Nos. 3,539,455 and 3,979,274 to Clark and Newman respectively. Enzyme electrodes are generally used to determine materials which themselves are not electrochemically active but which produce species which can be readily detected by the electrodes. In enzyme electrodes the enzymes are frequently located on polymeric membranes in close contact with the underlying electrode.

A considerable amount of research has been carried out in order to improve the properties of membranes for use in enzyme electrodes and many membranes for this purpose have been disclosed. An example of a type of membrane which is often used in the laminated membrane disclosed by Newman in U.S. Pat. No. 3,979,274. This membrane comprises a first or inner layer of an essentially homogenous material, for example cellulose acetate, which can prevent the passage of materials of even low molecular weight likely to interfere with the enzymic signal, a closely adherent layer of the enzynme itself (with or without such other materials that may be blended with it), and a second layer (in this instance an outer layer) of a porous support film which can prevent the passage of cellular and colloidal elements.

The determination of glucose can be taken as an example of the determination of a material by an enzyme electrode. In the presence of the enzyme glucose oxidase the following reaction occurs:

Glucose + $O_2$ $\xrightarrow{\text{glucose oxidase}}$ Gluconic acid + $H_2O_2$

The hydrogen peroxide produced in this reaction passes through the support film of a membrane such as that of U.S. Pat. No. 3,979,274 and can be determined using the electrode. Since the hydrogen peroxide produced is dependent upon the glucose present in a specimen, the glucose concentration can be determined using a suitably calibrated sensor.

To date a number of difficulties have limited the utility of enzyme electrodes and restricted the scale of their use in routine analysis of, e.g. blood samples. Two of these difficulties are as follows:

1. A tendency of components in physiological liquids, particularly blood, to block the pores or to coat the permeable surfaces of membranes and reduce the operational life-time of the membranes.

2. The limited linearity of the response of electrodes to analytes such as glucose or lactate which are substrates for the enzyme catalysed reactions. The response is linear only over a limited range of low concentrations of the analytes and hence the concentrations of the materials to be determined must be low and generally highly diluted samples must be used in specimens for analysis using enzyme electrodes. It is not always practicable to make diluted samples for routine analysis outside the laboratory and is impossible for in vivo monitoring.

According to the present invention we provide a membrane permeable to liquids and solutes which comprises one or more layers of polymeric material and at least one layer in which has been treated with a medium comprising an organosilane having reactive groups.

Further according to the invention we provide a method for treating a membrane which is permeable to liquids and solutes and comprises one or more layers of polymeric material wherein a medium comprising an organosilane having reactive groups is applied to at least one layer in the membrane.

Further according to the invention we provide a sensor of the enzyme-electrode type which incorporates a membrane permeable to liquids and solutes and comprising an enzyme and one or more layers of polymeric material and having an outer layer capable of being brought into contact with a specimen containing an analyte which is convertiable in the presence of the enzyme into a species which can be detected by the sensor wherein said outer layer and/or another layer between it and the enzyme has been treated with a medium comprising an organosilane having reactive groups.

Further according to the invention we provide a method for determining an analyte in a specimen which comprises contacting the specimen with the outer layer of a membrane, permeable to liquids and solutes and comprising an enzyme, in the presence of which the analyte is convertable into a species detectable by a sensor which incorporates the membrane, and one or more layers of polymeric material, and measuring the response of the sensor to the species, wherein said outer layer and/or another layer between it and the enzyme has been treated with a medium comprising an organosilane having reactive groups.

The main application of the membranes of the invention is in sensors of the enzyme-electrode type. However the membranes have other applications, in situations where membranes permeable to liquids and/or solutes are required, particularly medical applications. Examples of other medical applications of the membranes include use as dialysis membranes and as membranes used in implants or used to encapsulate cells.

The membrane of the invention may be used in any type of enzyme-electrode sensor. In its most simple form such a sensor consists of an enzyme-containing layer and a layer formed from polymeric material. The layer of polymeric material is the outer layer in this simple form of membrane and is contacted directly by the specimen in the method of the invention for determining an analyte.

However it is preferred that the membrane is a laminated membrane of the type of which that disclosed in U.S. Pat. No. 3,979,274 is an example. Such a membrane comprises a first or inner layer of polymeric material positioned between the enzyme-containing layer and the electrode, the enzyme-containing layer and a second layer of polymeric material on the other side of the enzyme-containing layer which second layer is usually the layer which is treated with the silane.

Hereafter in this specification the sensor of the invention which is described will contain a laminated membrane of the type of which the membrane described in U.S. Pat. No. 3,979,274 is an example having first and second layers, the layer treated with the silane being the second layer.

It should be understood that the membrane of the invention can contain more than two layers of polymeric material. For instance the second layer is not necessarily the outermost layer of the membrane. There may be a further layer or layers of polymeric material, i.e. third, fourth etc layers, between the second layer or layer of restricted permeability and the specimen. When the membrane comprises third and/or fourth polymeric layers it is not necessarily the outermost layer which is treated with the silane. It can be an inner, e.g. the second, layer. Often however the second layer will be the outer layer and its outer face will be treated with silane and will be contacted by the specimen. The membrane of the invention may be used as a detachable membrane or as an adherent membrane over a disposable sensor. Materials used in suitable sensors include noble metals and/or carbon.

The silanes used in the treatment method of the invention can have one or more silicon atoms in their molecules. Preferably silanes having two or more (especially three) reactive groups, particularly halide atoms such as chlorine atoms, are used. Other groups attached to the silicon atoms in addition to the reactive groups are suitably alkyl, particularly methyl, groups but other non-reactive groups, e.g. phenyl groups, are possible. Particularly suitable silanes are phenyltrichlorosilane and dimethyldichlorosilane and methyltrichlorosilane. The silane can be applied to the outer face of the outer layer of the membrane dropwise in a solvent. Suitable solvents are inert organic solvents which can evaporate readily, for example trichloroethane. Alternatively and more suitably the layer to be treated is immersed in the silane before the laminated membrane is formed and positioned upon the sensor. Thus either or both faces of the layer (e.g. the second layer) may be treated with silane. There are many possibilities for the formation of the silanated membrane for instance the enzyme can be immobilised, e.g. by cross-linking, directly onto the inner face of the silanated layer or alternatively it can be applied as a pre-formed film onto the inner face.

Suitable polymer materials for the second layer of a laminated membrane of the type disclosed in U.S. Pat. No. 3,979,274 include polycarbonates and modified cellulose, preferably polycarbonates. A very suitable modified cellulose membrane is a cellulose acetate/cellulose nitrate mixed ester ultrafiltration membrane. The second layer acts as a diffusion barrier which prevents or restricts the passage of compounds of high molecular weight and gives strength to the membrane sufficient to enable it to retain its shape and to maintain suitable contact with the electrode. Preferably the second layer has a thickness of less than 20 microns, especially within the range 1 to 10 microns. Suitably the polymeric material of the second layer has pores of average diameter within the range 1 micron to 0.05 microns or preferably lower as described in our co-pending UK Patent Application No. 8522834.

Suitable materials for the first layer of a laminated membrane include polymethyl-methacrylate, cellulose acetate, polyurethane or other polymeric materials which will restrict or prevent passage of electroactive interfering compounds such as ascorbic acid and tyrosine. Suitably the first layer has a thickness in the range 0.5 to 1.0 microns. Suitable materials include also materials which exclude any species over a pre-determined molecular weight, e.g. over 100 or particularly over 50.

The enzyme present in the sensor of the invention may be located on the membrane in any suitable manner. Preferably in a laminated membrane it is present between the two layers of polymeric material forming the bond between them. In this situation, and also generally, the enzyme is preferably immobilised by mixing with a material which causes cross linking to occur. A very suitable material for this purpose is glutaraldehyde but proteins such as albumin and other materials may also be included. In order to facilitate the obtaining of rapid stable readings from the sensor it is preferred that the enzyme-containing layer is thin, i.e. not greater than 5 microns thick.

The enzyme to be used in the sensor of the invention will depend upon the analyte whose concentration is to be determined. If the analyte is glucose then the enzyme will be glucose oxidase. Other enzymes which may be present include uricase and lactate oxidase for determinations of uric acid and lactic acid respectively.

The treatment method of the invention may for example be carried out using the following steps in order to produce a membrane for use in an enzyme electrode sensor for the determination of glucose:

1. The silane (e.g. dimethyldichlorosilane) is dissolved in a suitable solvent (e.g. 1-1-1-trichloroethane) to give a 2% solution:

2. Approximately 200 μg of the solution is added dropwise to a 1 cm$^2$ polycarbonate membrane positioned on a glass slide:

3. The solution is allowed to soak into the membrane for a few seconds:

4. The membrane is covered with a second glass slide and the two slides are clamped together for 5 minutes during which time some polymerisation of the silane occurs:

5. The membrane is removed from the slides and rinsed in a jet of water to hydrolyse any unreacted groups:

6. The membrane is dried in air:

7. 1 mg glucose oxidase is dissolved in 50 μl of (100 mg/ml) albumen:

8. 3 μl of 12.5% glutaraldehyde solution is mixed with 3 1 of the enzyme/albumen mixture on a glass microscope slide:

9. 1 μl of the mixture produced in the previous step is placed on one face of the membrane:

10. The upper surface of the enzyme layer is covered immediately with a thin cellulose acetate membrane and the resulting laminated membrane is clamped for 3 minutes between glass slides. After removal from the glass slides the laminated membrane produced by the above sequence of steps may be used on a platinum electrode with the cellulose acetate membrane nearest to the electrode.

The membranes of the invention have the general advantage that the treatment with organosilane reduces the tendency for the surfaces of the membranes to become fouled by clotted blood. This is an advantage whenever the membranes are used in circumstances in which they are contacted by blood as in the diafiltration treatment of kidney patients. Dialysis membranes similarly treated with organosilane have also a reduced tendency to surface fouling, this is an advantage when such membranes are contacted by blood during haemodialysis. When the membranes are used in sensors for determining components of blood they can be used a greater number of times because of the reduced tendency for the surface to be coated or blocked by proteins and cellular constituents. This makes sensors incorporating the treated membranes more useful in routine analysis of blood.

When the treated membranes of the invention are used in sensors there is the further advantage of an increase in the concentration range over which a graph of concentration against sensor response is linear. With untreated membranes linearity extends only up to approximately a concentration of 3 mM for glucose. With treated membranes linearity is increased and the range extends to glucose concentrations of 50 mM and even higher. This is achieved through restriction of substrate entry into the enzyme layer and therefore with some loss of sensitivity. Thus the range can be made to cover the concentrations of glucose which can be anticipated in blood samples thus enabling blood glucose levels to be determined more readily. This is a considerable advantage in situations where large numbers of determinations must be made regularly and with minimal sample preparation.

In addition to their medical uses the enzyme-electrode sensors have a number of other uses including industrial fermentation medium monitoring, laboratory based fermentation medium monitoring and veterinary in vivo and in vitro applications.

The invention is illustrated by the following Examples.

EXAMPLE 1

A laminated membrane was fabricated using the treatment described in steps 1 to 10 above and was placed over the surface of a polarographic electrode system with its working (platinum) electrode poised at +0.6 V with respect to a silver reference electrode. The resulting membrane-coated electrode system is shown in cross-section in FIG. 1 of the drawings. In FIG. 1, reference numeral 1 is a second or outer layer formed from a 0.05 micron pore size polycarbonate film coated with dimethyldichlorosilane, 2 is a layer of glucose oxidase enzyme dissolved in albumen and mixed with glutaraldehyde, 3 is a first or inner layer formed from cellulose acetate, 4 is the platinum working electrode and 5 is the silver pseudo-reference electrode. Platinum working electrode 4 acts as an anode whilst silver pseudo-reference electrode 5 acts as a cathode. The membrane is held in place on the electrode by a perspex ring pressing down on second layer 1 towards its outer edges at 6.

The membrane was first moistened with glucose-free electrolyte (0.9% NaCl solution) to provide a base-line current. A series of aqueous standard glucose solutions of differing concentrations were then applied, each in turn as a single drop to cover working electrode 4. Stable readings were taken for each standard solution. Between each analysis the membrane surface was rinsed with buffer and dabbed with filter paper to remove excess liquid.

Figure 2:
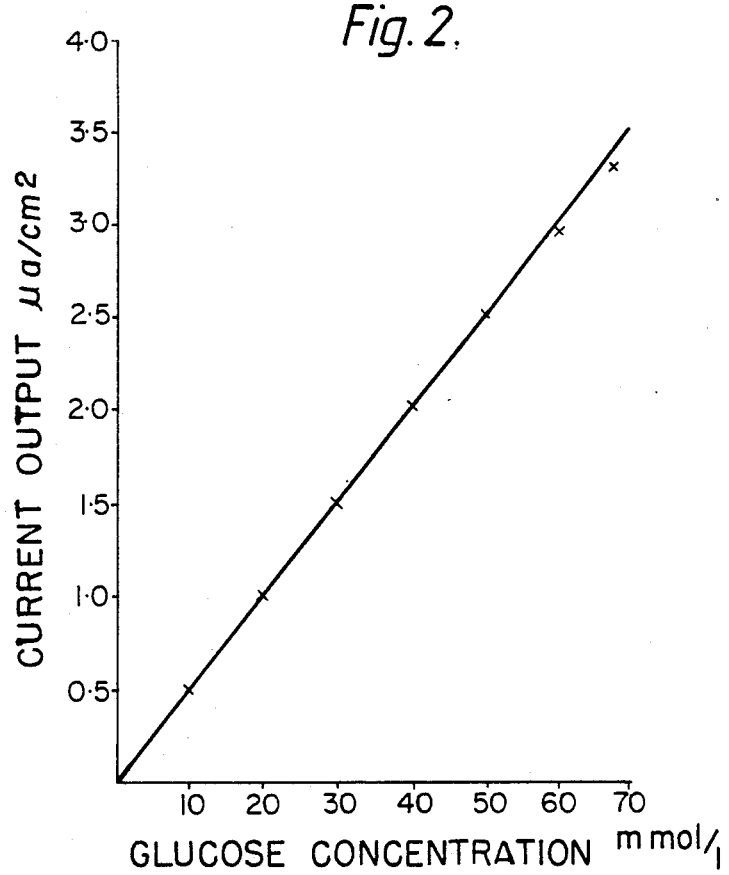

The stable readings obtained with the glucose solution were used to construct the calibration graph shown in FIG. 2 of the drawings. In this calibration graph the ordinate is the current output in microamps per square cm and the abscissa is the concentration of glucose in m mol/1.

It can be seen from the calibration graph of FIG. 2 that the graph is linear at least to concentrations of glucose of 50 m mol/1. This covers the concentration range which is clinically important.

EXAMPLE 2

A laminated membrane was prepared in a manner similar to that described in Example 1 except that the second or outer layer 1 in FIG. 1 was formed from a 0.2$\mu$ pore size polyester membrane manufactured by Nucleopore and treated with methyltrichlorosilane in the same manner as described above using dimethyldichlorosilane.

A calibration graph was constructed as described in Example 1 using measurements made with a number of glucose solutions of differing concentrations. In this instance the graph is near-linear up to 8 mM. This is a marked improvement compared to the results achieved using a similarly constructed control membrane in which the second layer was not silinated and with which there was no significant increase in response to glucose concentrations above 2 mM.

Figure 3:
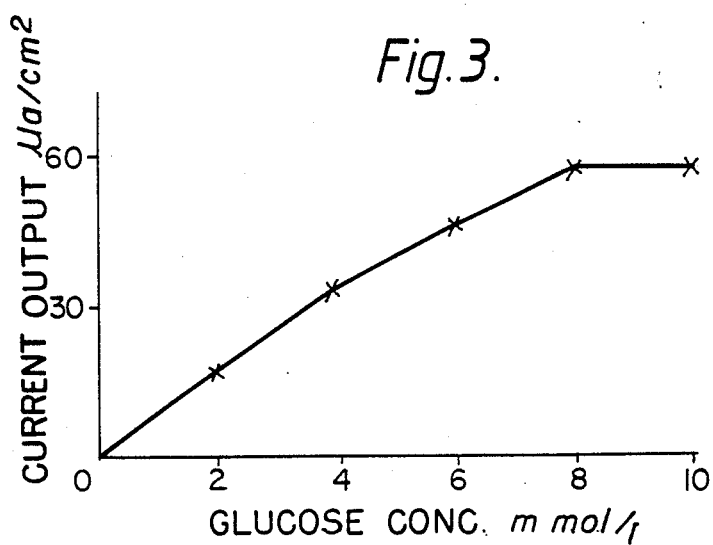

The calibration graph is shown in FIG. 3 of the drawings. In it the ordinate is current output in microamps per cm$^2$ and the abscissa is the glucose concentration in m mol/1.

EXAMPLE 3

A laminated membrane was prepared in a manner similar to that described in Example 1 except that the second or outer layer 1 in FIG. 1 was formed from a 0.05$\mu$ pore size polycarbonate membrane which was treated with methyltrichlorosilane using the method described above for treatments with dimethyldichlorosilane.

A calibration graph was constructed as described in Example 1 using measurements made with a number of glucose solutions of differing concentrations. In this instance the graph is linear up to 10 mM (and possibly higher if measurements had been continued). This is a marked improvement upon the results achieved using (a) a membrane of the type described in U.S. Pat. No. 3,979,274 and a control membrane in which the second layer was not silanated. With both the membrane of U.S. Pat. No. 3,979,274 and the control there was no sigificant increase in response to glucose concentrations above 2 mM.

Figure 4:
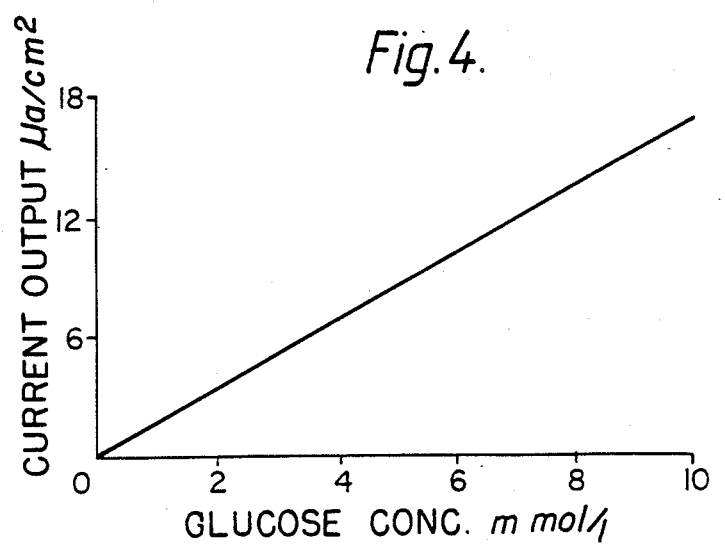

The calibration graph is shown in FIG. 4 of the drawings in which the co-ordinates are the same as in FIGS. 2 and 3.

EXAMPLE 4

Silanated, laminated membranes were produced using the treatment described above and using a series of silanes. Measurements were made using a series of glucose solutions and the maximum extent of linearity for each different silane was measured. The results are set out in Table 1. A control membrane which had not been treated with silane gave a maximum linearity of 5 mM.

The maximum linearity varies depending upon the silane employed. In two instances very high maximum linearities were observed. Such linearities are considerably beyond the range required for medical applications. They are however useful in certain industrial applications for example measuring the concentration of glucose in a fermenter.

TABLE 1

| Silane | Maximum glucose concentration (mM) up to which response was linear |
| --- | --- |
| Methyltrichlorosilane | 500 |
| Phenyltrichlorosilane | 500 |
| Dimethyldichlorosilane | 70 |
| Methyldichlorosilane | 50 |
| No silane treatment | 5 |

EXAMPLE 5

The effect of blood on the sensitivity of an enzyme electrode sensor was studied by examining the responses of an enzyme electrode to whole diluted blood. The responses were studied (a) when the electrode was coated with an enzyme cross-linked to plasma protein but otherwise left uncovered, (b) when the enzyme layer was covered with a smooth layer of "CUPROPHAN" (Registered Tade Mark) modified cellulose polymer, and (c) when the enzyme layer was covered with a layer of "CUPROPHAN" treated with methyltrichlorosilane. The first polymer layer underlying the enzyme layer was an unselective film since for these studies only the loss of response was of interest. The blood used was diluted 1 in 50 and assayed in stirred phosphate buffer (pH 7.4). Determinations were made using a 10μ mol/1 glucose standard solution.

The results are given in Table 2. It can be seen from this table that in (a) above the loss of response was extremely rapid whilst in (b) above it was less rapid. Using the silane treated membrane of (c) above however the loss of response was greatly diminished.

TABLE 2

| | Covering Membrane | Time in whole diluted blood (mins) | Loss of Response |
| --- | --- | --- | --- |
| (a) | none | 3 | 7% |
| (b) | untreated "CUPROPHAN" | 20 | 9% |
| (c) | silane treated "CUPROPHAN" | 5 | 0% |
| | | 20 | 2% |

I claim:

1. A sensor of the enzyme-electrode type, comprising a sensor and a membrane thereon which is permeable to liquids and solutes, wherein the membrane comprises a first layer of polymeric material forming that face of the membrane which is nearer to the sensor, an enzyme-containing layer, and at least one further layer of polymeric material on that side of the enzyme-containing layer which is remote from said first layer, at least one of said at least one further layers being of a type which has been treated by being exposed to contact with a medium containing an organosilane.

2. A sensor according to claim 1, wherein the organosilane contains in the molecule at least one group which is reactive to polymerize the organosilane.

3. A sensor of the enzyme-electrode type, comprising:
   a sensor; and
   a membrane thereon which is permeable to liquids and solutes,
   wherein the membrane comprises a first layer of a polymeric material selected from the group comprising polymethyl methacrylate, polyurethane, cellulose acetate and other polymeric materials restricting the passage of electroactive interfering compounds,
   an enzyme-containing layer disposed on that side of the first layer which is remote from the sensor, and
   a second layer of polymeric material disposed on that side of the enzyme-containing layer which is remote from the first layer, said second layer being of a polymeric material selected from the group comprising polycarbonates and modified cellulose, said second layer of a type which has been treated by being exposed to contact with an organosilane having at least one halogen-containing group.

4. A sensor according to claim 3, wherein said organosilane is selected from the group comprising phenyltrichlorosilane, dimethyldichlorosilane and methyltrichlorosilane.

5. A sensor according to claim 3, wherein the polymeric material of said second layer has pores of average diameter less than 0.05 microns.

6. A method for determining an analyte in a specimen, said method including the steps of contacting said specimen with the outermost layer of a membrane of an enzyme-electrode type sensor, and measuring the response of said sensor to species that are formed from said analyte by said enzyme,
   wherein the improvement comprises said membrane that is permeable to liquids and solutes and which includes
   (i) a first layer of polymeric material forming that face of the membrane which is nearest said sensor;
   (ii) a layer containing said enzyme; and
   (iii) at least one second layer of polymeric material, at least one of said at least one second layers having been exposed to contact with a medium containing an organosilane, wherein at least one of said organosilane contacted layers lies between said enzyme-containing layer and said specimen.

* * * * *